(12) United States Patent
Wendlinger et al.

(10) Patent No.: US 11,034,635 B2
(45) Date of Patent: Jun. 15, 2021

(54) PROCESS FOR THE PRODUCTION OF 2,3,3,3-TETRAFLUOROPROPENE

(71) Applicant: Arkema France, Colombes (FR)

(72) Inventors: Laurent Wendlinger, Pierre-Benite (FR); Dominique Deur-Bert, Pierre-Benite (FR); Anne Pigamo, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/976,819

(22) PCT Filed: Mar. 4, 2019

(86) PCT No.: PCT/FR2019/050477
§ 371 (c)(1),
(2) Date: Aug. 31, 2020

(87) PCT Pub. No.: WO2019/170989
PCT Pub. Date: Sep. 12, 2019

(65) Prior Publication Data
US 2020/0407293 A1    Dec. 31, 2020

(30) Foreign Application Priority Data
Mar. 7, 2018    (FR) .................................. 1851956

(51) Int. Cl.
*C07C 17/20* (2006.01)
*C07C 17/25* (2006.01)
*C07C 21/18* (2006.01)

(52) U.S. Cl.
CPC ............ *C07C 17/206* (2013.01); *C07C 17/25* (2013.01); *C07C 21/18* (2013.01)

(58) Field of Classification Search
CPC ........ C07C 21/18; C07C 17/206; C07C 17/25
See application file for complete search history.

(56) References Cited

U.S. PATENT DOCUMENTS

| | | | |
|---|---|---|---|
| 2,773,014 A | 12/1956 | Snuggs et al. | |
| 4,902,838 A | 2/1990 | Manzer et al. | |
| 5,227,350 A | 7/1993 | Scott et al. | |
| 5,322,597 A | 6/1994 | Childs et al. | |
| 5,334,784 A | 8/1994 | Blake et al. | |
| 5,919,728 A | 7/1999 | Rinaldi et al. | |
| 8,614,361 B2 | 12/2013 | Suzuki et al. | |
| 8,618,338 B2 | 12/2013 | Elsheikh et al. | |
| 9,255,045 B2 | 2/2016 | Pigamo et al. | |
| 9,340,473 B2 | 5/2016 | Pigamo et al. | |
| 9,708,234 B2 | 7/2017 | Chaki et al. | |
| 9,834,499 B2 | 12/2017 | Pigamo et al. | |
| 10,227,275 B2 | 3/2019 | Pigamo et al. | |
| 10,427,998 B2 | 10/2019 | Pigamo et al. | |
| 10,532,965 B2 | 1/2020 | Pigamo et al. | |
| 2009/0240090 A1 | 9/2009 | Merkel et al. | |
| 2009/0287026 A1 | 11/2009 | Kopkalli et al. | |
| 2010/0191025 A1 | 7/2010 | Perdrieux | |
| 2011/0031436 A1 | 2/2011 | Mahler et al. | |
| 2013/0197281 A1 | 8/2013 | Hintzer et al. | |
| 2013/0267740 A1 | 10/2013 | Wendlinger et al. | |
| 2014/0012051 A1 | 1/2014 | Pigamo et al. | |
| 2014/0039228 A1 | 2/2014 | Pigamo et al. | |
| 2014/0275653 A1* | 9/2014 | Pigamo ................... C07C 21/18 570/160 |
| 2015/0008357 A1 | 1/2015 | Furuta et al. | |
| 2015/0197467 A1 | 7/2015 | Pigamo et al. | |
| 2016/0115104 A1 | 4/2016 | Pigamo et al. | |
| 2016/0237009 A1 | 8/2016 | Deur-Bert et al. | |
| 2017/0158586 A1 | 6/2017 | Collier et al. | |
| 2017/0210686 A1 | 7/2017 | Pigamo et al. | |
| 2018/0093934 A1 | 4/2018 | Pigamo et al. | |
| 2018/0148394 A1 | 5/2018 | Pigamo et al. | |
| 2019/0127303 A1 | 5/2019 | Ondrus et al. | |
| 2019/0152883 A1 | 5/2019 | Pigamo et al. | |
| 2019/0375698 A1 | 12/2019 | Pigamo et al. | |

(Continued)

FOREIGN PATENT DOCUMENTS

| CN | 107540011 A | 1/2018 |
|---|---|---|
| EP | 0 449 617 A2 | 10/1991 |
| EP | 0582192 A1 | 2/1994 |

(Continued)

OTHER PUBLICATIONS

International Search Report (PCT/ISA/210) and translation and Written Opinion (PCT/ISA/237) dated Jun. 26, 2019, by the European Patent Office as the International Searching Authority for International Application No. PCT/FR2019/050478.
International Search Report (PCT/ISA/210) dated Jun. 6, 2019, by the French Patent Office as the International Searching Authority for International Application No. PCT/FR2019/050479.
Written Opinion (PCT/ISA/237) dated Jun. 6, 2019, by the French Patent Office as the International Searching Authority for International Application No. PCT/FR2019/050479.
Bonnet, "Liquid-phase HF Fluorination", Multiphase Homogeneous Catalysis, 5.2 State of the Art, 2002 (month unknown), pp. 535-542.
International Search Report (PCT/ISA/210) dated Jun. 19, 2019, by the European Patent Office as the International Searching Authority for International Application No. PCT/FR2019/050477.
Written Opinion (PCT/ISA/237) dated Jun. 19, 2019, by the European Patent Office as the International Searching Authority for International Application No. PCT/FR2019/050477.

(Continued)

*Primary Examiner* — Jafar F Parsa
(74) *Attorney, Agent, or Firm* — Buchanan Ingersoll & Rooney P.C.

(57) ABSTRACT

The present invention relates to a process for producing 2,3,3,3-tetrafluoropropene, comprising the steps of: a) providing a stream A comprising at least one of the compounds selected from the group consisting of 2-chloro-3,3,3-trifluoropropene and 2,3-dichloro-1,1,1-trifluoropropane; b) in a reactor, bringing said stream A into contact with HF in the presence or absence of a fluorination catalyst in order to produce a stream B comprising 2,3,3,3-tetrafluoropropene; characterized in that the electrical conductivity of said stream A provided in step a) is less than 15 mS/cm.

10 Claims, No Drawings

(56) References Cited

U.S. PATENT DOCUMENTS

| | | | |
|---|---|---|---|
| 2021/0002188 A1 | 1/2021 | Wendlinger et al. | |
| 2021/0002189 A1 | 1/2021 | Wendlinger et al. | |

FOREIGN PATENT DOCUMENTS

| | | | |
|---|---|---|---|
| EP | 0 939 071 A1 | 9/1999 | |
| FR | 3 013 606 | 5/2015 | |
| WO | 0181353 A1 | 11/2001 | |
| WO | 2007079431 A2 | 7/2007 | |
| WO | WO 2008/040969 A2 | 4/2008 | |
| WO | WO 2008/054781 A1 | 5/2008 | |
| WO | 2008149011 A2 | 12/2008 | |
| WO | WO 2009/118628 A1 | 10/2009 | |
| WO | 2009137658 A2 | 11/2009 | |
| WO | 2011077192 A1 | 6/2011 | |
| WO | 2012012113 A1 | 1/2012 | |
| WO | 2012052797 A1 | 4/2012 | |
| WO | WO 2012/098421 A1 | 7/2012 | |
| WO | WO 2012/098422 A1 | 7/2012 | |
| WO | 2013088195 A1 | 6/2013 | |
| WO | WO 2013/154059 A1 | 10/2013 | |
| WO | WO 2013/182816 A1 | 12/2013 | |
| WO | WO 2014/010750 A1 | 1/2014 | |
| WO | 2017178857 A1 | 10/2017 | |

OTHER PUBLICATIONS

Mukerjee, Pasupati, et al., "Effect of temperature on the electrical conductivity and the thermodynamics of micelle formation of sodium perfluorooctanoate", Journal of Physical Chemistry, vol. 89, No. 21, Nov. 1, 1985, pp. 5308-5312.

U.S. Appl. No. 17/251,328, Hisler et al.

Hisler, Kevin, et al., U.S. Appl. No. 17/251,328, entitled "Method for Producing 1-Chloro-3,3,3-Trifluoropropene," filed in the U.S. Patent and Trademark Office on Dec. 11, 2020.

U.S. Appl. No. 17/053,250, Pigamo et al.

International Search Report (PCT/ISA/210) and Written Opinion (PCT/ISA/237), issued in PCT/FR2015/051653, dated Sep. 1, 2015, European Patent Office, Rijswijk, NL, 19 pages.

Wendlinger, Laurent, et al., U.S. Appl. No. 16/976,520, entitled "Process for Producing 2-Chloro-3,3,3-Trifluoropropene," filed in the U.S. Patent and Trademark Office on Aug. 28, 2020.

Wendlinger, Laurent, et al., U.S. Appl. No. 16/976,599, entitled "Process for the Production of 2,3,3,3-Tetrafluoropropene," filed in the U.S. Patent and Trademark Office on Aug. 28, 2020.

Pigamo, Anne, et al., U.S. Appl. No. 17/053,250 entitled "Method for Producing 1-Chloro-3,3,3-Trifluoropropene," filed in the U.S. Patent and Trademark Office on Nov. 5, 2020.

**Boutier, Jean-Christophe, et al., et al., U.S. Appl. No. 17/280,547, entitled "Stabilization of 1-Chloro-3,3,3-Trifluoropropene," filed in the U.S. Patent and Trademark Office dated Mar. 26, 2021.

* cited by examiner

PROCESS FOR THE PRODUCTION OF 2,3,3,3-TETRAFLUOROPROPENE

TECHNICAL FIELD OF THE INVENTION

The present invention relates to the production of hydrofluoroolefins. More particularly, the present invention relates to the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds having a structure which is useful as functional materials, solvents, refrigerants, blowing agents and monomers for functional polymers or starting materials for such monomers. Hydrofluoroolefins, such as 2,3,3,3-tetrafluoropropene (HFO-1234yf), are attracting attention because they offer promising behavior as refrigerants having a low global warming potential.

Processes for producing fluoroolefins are usually performed in the presence of a starting substance, such as a chlorine-containing alkane or a chlorine-containing alkene, and in the presence of a fluorinating agent, such as hydrogen fluoride. These processes may be performed in the gas phase or in the liquid phase, in the absence or presence of a catalyst.

For example, US 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2011/077192 also discloses a process for the preparation of 2,3,3,3-tetrafluoropropene comprising in particular a step in which 2-chloro-3,3,3-trifluoropropene is brought into contact with HF in the gas phase in the presence of a fluorination catalyst.

There is still a need for more effective processes for the production of 2,3,3,3-tetrafluoropropene.

SUMMARY OF THE INVENTION

The present invention relates to a process for the production of 2,3,3,3-tetrafluoropropene comprising the steps:

a) providing a stream A comprising at least one starting compound selected from the group consisting of 2-chloro-3,3,3-trifluoropropene and 2,3-dichloro-1,1,1-trifluoropropane, b) in a reactor, bringing said stream A into contact with HF in the presence or absence of a catalyst in order to produce a stream B comprising 2,3,3,3-tetrafluoropropene, characterized in that the electrical conductivity of said stream A provided in step a) is less than 15 mS/cm.

The present process makes it possible to optimize and improve the production of 2,3,3,3-tetrafluoropropene. An electrical conductivity value of less than 15 mS/cm for the stream A before the implementation of the fluorination and/or dehydrofluorination step makes it possible to guarantee an optimal effectiveness of the reaction in terms of conversion and of selectivity. If a catalyst is present, such a value makes it possible to also guarantee an optimal effectiveness the catalyst.

According to a preferred embodiment, step b) is carried out in the gas phase in the presence of a catalyst.

According to a preferred embodiment, the electrical conductivity of said stream A is less than 10 mS/cm.

According to a preferred embodiment, step b) is carried out in the presence of a chromium-based catalyst; in particular, said catalyst comprises a chromium oxyfluoride or a chromium oxide or a chromium fluoride or a mixture of these.

According to a preferred embodiment, the catalyst is based on chromium and also comprises a cocatalyst selected from the group consisting of Ni, Zn, Co, Mn and Mg; preferably, the content of cocatalyst is between 0.01% and 10%, based on the total weight of the catalyst.

According to a preferred embodiment, stream A comprises 2-chloro-3,3,3-trifluoropropene, HF and optionally 1,1,1,2,2-pentafluoropropane.

According to a preferred embodiment, in addition to 2,3,3,3-tetrafluoropropene, stream B comprises HF, HCl, 2-chloro-3,3,3-trifluoropropene which has not reacted and optionally 1,1,1,2,2-pentafluoropropane.

According to a preferred embodiment, step b) is carried out at a temperature of between 310° C. and 420° C.

According to a preferred embodiment, step b) is carried out in the presence of hydrofluoric acid having an electrical conductivity of less than 10 mS/cm.

DETAILED DESCRIPTION OF THE PRESENT INVENTION

The present invention relates to a process for the production of 2,3,3,3-tetrafluoropropene comprising the steps:

a) providing a stream A comprising at least one of the compounds selected from the group consisting of 2-chloro-3,3,3-trifluoropropene and 2,3-dichloro-1,1,1-trifluoropropane, b) in a reactor, bringing said stream A into contact with HF in the presence or absence of a catalyst in order to produce a stream B comprising 2,3,3,3-tetrafluoropropene.

According to a preferred embodiment, the electrical conductivity of said stream A provided in step a) is less than 15 mS/cm. Advantageously, the electrical conductivity of said stream A provided in step a) is less than 14 mS/cm, preferably less than 13 mS/cm, more preferentially less than 12 mS/cm, in particular less than 11 mS/cm, more particularly less than 10 mS/cm, favorably less than 9 mS/cm, advantageously favorably less than 8 mS/cm, preferentially favorably less than 7 mS/cm, more preferentially favorably less than 6 mS/cm, particularly favorably less than 5 mS/cm. The electrical conductivity is measured using an inductive conductivity measurement cell according to the practice known to a person skilled in the art. The electrical conductivity is measured at ambient temperature. The electrical conductivity is measured at a pressure equal to the pressure at which step b) is carried out. The electrical conductivity of the stream A can be reduced, in order to achieve a conductivity of less than 15 mS/cm, by reducing the concentration of electrolyte possibly present in the stream according to techniques known to a person skilled in the art (distillation, cooling and separation by settling, passage through 3 to 5 Å molecular sieves or zeolites). Preferably, the measurement cell is coated with a material resistant to a corrosive medium, in particular resistant to hydrofluoric acid.

The electrical conductivity of said stream A is measured prior to step b). Preferably, the electrical conductivity of said stream A is measured when the latter is in liquid form. Said process according to the present invention can thus comprise a step of heating and vaporization of said stream A prior to the implementation of step b) in order to provide said stream A in gaseous form. Preferably, said stream A employed in step b) is in gaseous form during the contacting thereof with HF.

According to a preferred embodiment, step b) is carried out in the presence of a catalyst, preferably a chromium-based catalyst. Preferably, the chromium-based catalyst can be a chromium oxide (for example $CrO_2$, $CrO_3$ or $Cr_2O_3$), a chromium oxyfluoride or a chromium fluoride (for example $CrF_3$) or a mixture of these. The chromium oxyfluoride can contain a fluorine content of between 1% and 60% by weight, based on the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight of fluorine, based on the total weight of the chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1% and 10% by weight, based on the total weight of the catalyst. The catalyst may or may not be supported. A support, such as alumina, activated alumina, aluminum halides ($AlF_3$, for example), aluminum oxyhalides, activated carbon, magnesium fluoride or graphite, can be used.

Preferably, the catalyst can have a specific surface area of between 70 and 225 $m^2/g$, advantageously between 90 and 200 $m^2/g$, preferably between 100 and 190 $m^2/g$, in particular between 125 and 180 $m^2/g$. Alternatively, the catalyst can have a specific surface area of between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to a preferred embodiment, the pressure at which step b) is carried out is atmospheric pressure or a pressure greater than atmospheric pressure; the pressure at which step b) is carried out is advantageously greater than 1.5 bara, preferably greater than 2.0 bara, in particular greater than 2.5 bara, more particularly greater than 3.0 bara. Preferably, step b) is carried out at a pressure of between atmospheric pressure and 20 bara, preferably between 2 and 18 bara, more preferentially between 3 and 15 bara.

Preferably, step b) of the present process is carried out with a contact time of between 1 and 100 s, preferably between 2 and 75 s, in particular between 3 and 50 s. Preferably, the molar ratio of HF to said at least one of the compounds of said stream A. i.e. 2-chloro-3,3,3-trifluoropropene or 2,3-dichloro-1,1,1-trifluoropropane, may range between 1:1 and 150:1, preferably between 2:1 and 125:1, more preferentially between 3:1 and 100:1. An oxidant, such as oxygen or chlorine, can be added during step b). The molar ratio of the oxidant to the hydrocarbon compound can be between 0.005 and 2, preferably between 0.01 and 1.5. The oxidant may be pure oxygen, air, or a mixture of oxygen and nitrogen.

According to a preferred embodiment, step b) is carried out at a temperature of between 310° C. and 420° C., advantageously between 310° C. and 400° C., preferably between 310° C. and 375° C., more preferentially between 310° C. and 360° C., in particular between 330° C. and 360° C.

According to a preferred embodiment, stream A comprises 2-chloro-3,3,3-trifluoropropene or 2,3-dichloro-1,1,1-trifluoropropane, HF and optionally 1,1,1,2,2-pentafluoropropane.

According to a preferred embodiment, in addition to 2,3,3,3-tetrafluoropropene, stream B comprises HF, HCl, 2-chloro-3,3,3-trifluoropropene or 2,3-dichloro-1,1,1-trifluoropropane which has not reacted and optionally 1,1,1,2,2-pentafluoropropane.

According to a preferred embodiment, stream B is purified, preferably by distillation, in order to form a first stream comprising 2,3,3,3-tetrafluoropropene, HCl and optionally 1,1,1,2,2-pentafluoropropane and a second stream comprising HF and 2-chloro-3,3,3-trifluoropropene or 2,3-dichloro-1,1,1-trifluoropropane.

Preferably, said stream B is distilled under conditions which are sufficient to form said first stream comprising 2,3,3,3-tetrafluoropropene, HCl and 1,1,1,2,2-pentafluoropropane and said second stream comprising HF and 2-chloro-3,3,3-trifluoropropene. In particular, the distillation can be carried out at a pressure of 2 to 6 bara, more particularly at a pressure of 3 to 5 bara. In particular, the temperature at the distillation column top is from −35° C. to 10° C., preferably from −20° C. to 0° C.

According to a preferred embodiment, said stream B obtained in step b) is cooled prior to the abovementioned purification. In particular, said stream B obtained in step b) is cooled to a temperature of less than 100° C., then distilled in order to form said first stream comprising 2,3,3,3-tetrafluoropropene, HCl and 1,1,1,2,2-pentafluoropropane, and said second stream comprising HF and 2-chloro-3,3,3-trifluoropropene or 2,3-dichloro-1,1,1-trifluoropropane; the temperature at the distillation column top is from −35° C. to 10° C. and the distillation is carried out at a pressure of 2 to 6 bara.

Said stream B can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the flow of products obtained to such temperatures can facilitate the subsequent distillation.

The cooling of said stream B can be carried out by means of one or a plurality of heat exchangers. The cooling of said stream B can be carried out by passing the latter through one, two, three, four, five, six, seven, eight, nine or ten heat exchangers; preferably, the number of heat exchangers is between 2 and 8, in particular between 3 and 7.

According to a preferred embodiment, step b) is carried out in the presence of hydrofluoric acid having an electrical conductivity of less than 10 mS/cm, preferably of less than 5 mS/cm. The electrical conductivity of the hydrofluoric acid can be measured prior to its use in step b) of the present process. Preferably, the electrical conductivity of the hydrofluoric acid is measured prior to step b) and the hydrofluoric acid is in liquid form during the measurement. The process can also comprise a step of heating and of vaporization of the hydrofluoric acid prior to the implementation of step b) in order to provide hydrofluoric acid in gaseous form. Preferably, the hydrofluoric acid is in gaseous form during the contacting with said stream A.

Preferably, the process according to the present invention is carried out continuously.

Example

The fluorination of HCFO-1233xf (2-chloro-3,3,3-trifluoropropene) to give HFO-1234yf (2,3,3,3-tetrafluoropropene) and optionally to give HFC-245cb (1,1,1,2,2-pentafluoropropane) is carried out in a multitubular reactor. The reactor contains a bulk catalyst based on chromium oxide. The catalyst is activated by a series of stages comprising drying, fluorination, treatment under air and fluorination with recycling. This multistage treatment makes it possible to render the catalytic solid active and selective.

The fluorination process is carried out according to the following operating conditions:
- an absolute pressure in the fluorination reactor of 5.8 bar absolute
- a molar ratio of the HF to the sum of the organic materials fed by the recycling loop of between 15 and 20
- a contact time of 16 seconds
- a constant temperature in the reactor of 350° C.

The process is carried out with a stream of HCFO-1233xf having three different electrical conductivity values: 6, 10 and 35 mS/cm. The electrical conductivity was measured at ambient temperature and at 5.8 bara. The run is halted when the conversion of 2-chloro-3,3,3-trifluoropropene is less than 50%. The values obtained are summarized in table 1 below.

The electrical conductivity of the stream of HCFO-1233xf is measured using a cell sold by Endress+Hauser and referenced by the term InduMax P CLS 50 coated with a polymer coating of perfluoroalkoxy (PFA) type resistant to a corrosive medium containing HF.

TABLE 1

| Example | Electrical conductivity (mS/cm) | Duration of the run to reach a conversion <50% (h) |
|---|---|---|
| 1 (inv.) | 6 | 400 |
| 2 (inv.) | 10 | 240 |
| 3 (comp.) | 35 | 40 |

The results given in detail in table 1 demonstrate that a stream comprising HCFO-1233xf and having an electrical conductivity of less than 15 mS/cm makes it possible to maintain a sufficiently high conversion for a significant period of time. This is because a conversion of greater than 50% can be maintained for more than 240 h (example 2) and even for up to 400 h when the electrical conductivity is 6 mS/cm (example 1). In contrast, the conversion of HCFO-1233xf falls strongly when the electrical conductivity is too high (example 3).

The invention claimed is:

1. A process for producing 2,3,3,3-tetrafluoropropene, comprising the steps of:
    a) providing a stream A comprising at least one starting compound selected from the group consisting of 2-chloro-3,3,3-trifluoropropene and 2,3-dichloro-1,1,1-trifluoropropane;
    b) in a reactor, bringing said stream A into contact with HF in the presence or absence of a catalyst in order to produce a stream B comprising 2,3,3,3-tetrafluoropropene;
    wherein the electrical conductivity of said stream A provided in step a) is less than 15 mS/cm.

2. The process as claimed in claim 1, wherein step b) is carried out in the gas phase in the presence of a catalyst.

3. The process as claimed in claim 1, wherein the electrical conductivity of said stream A is less than 10 mS/cm.

4. The process as claimed in claim 1, wherein step b) is carried out in the presence of a chromium-based catalyst.

5. The process as claimed in claim 1, wherein the catalyst is based on chromium and also comprises a cocatalyst selected from the group consisting of Ni, Zn, Co, Mn and Mg.

6. The process as claimed in claim 1, wherein stream A comprises 2-chloro-3,3,3-trifluoropropene, HF and 1,1,1,2,2-pentafluoropropane.

7. The process as claimed in claim 1, wherein, in addition to 2,3,3,3-tetrafluoropropene, stream B comprises HF, HCl, 2-chloro-3,3,3-trifluoropropene which has not reacted and 1,1,1,2,2-pentafluoropropane.

8. The process as claimed in claim 1, wherein step b) is carried out at a temperature of between 310° C. and 420° C.

9. The process as claimed in claim 1, wherein step b) is carried out in the presence of hydrofluoric acid having an electrical conductivity of less than 10 mS/cm.

10. The process as claimed in claim 1, wherein the process further comprises a step of reducing the concentration of electrolytes in stream A until the electrical conductivity of stream A is less than 15 mS/cm.

* * * * *